(12) United States Patent
Chung

(10) Patent No.: US 11,963,667 B2
(45) Date of Patent: Apr. 23, 2024

(54) ENDOSCOPIC IMAGE CAPTURING ASSEMBLY AND ENDOSCOPIC DEVICE THEREWITH

(71) Applicant: ALTEK BIOTECHNOLOGY CORPORATION, Hsinchu (TW)

(72) Inventor: Te-Yu Chung, Hsinchu (TW)

(73) Assignee: ALTEK BIOTECHNOLOGY CORPORATION, Hsinchu (TW)

( * ) Notice: Subject to any disclaimer, the term of this patent is extended or adjusted under 35 U.S.C. 154(b) by 0 days.

(21) Appl. No.: 17/535,696

(22) Filed: Nov. 26, 2021

(65) Prior Publication Data

US 2023/0165449 A1  Jun. 1, 2023

(51) Int. Cl.
*A61B 1/05* (2006.01)
*A61B 1/00* (2006.01)
*A61B 1/06* (2006.01)

(52) U.S. Cl.
CPC ............ *A61B 1/05* (2013.01); *A61B 1/00114* (2013.01); *A61B 1/00121* (2013.01); *A61B 1/00147* (2013.01); *A61B 1/0661* (2013.01)

(58) Field of Classification Search
CPC ............ A61B 1/00009; A61B 1/00096; A61B 1/00105; A61B 1/00114; A61B 1/00121; A61B 1/0147; A61B 1/05; A61B 1/0114; A61B 1/0121; A61B 1/0661; A61B 1/051
See application file for complete search history.

(56) References Cited

U.S. PATENT DOCUMENTS

| 5,365,268 A * | 11/1994 | Minami | H04N 23/54 |
| | | | 257/E31.118 |
| 6,494,739 B1 * | 12/2002 | Vivenzio | H01R 13/5804 |
| | | | 358/473 |
| 2007/0182842 A1 | 8/2007 | Sonnenschein | |
| 2011/0118549 A1 | 5/2011 | Han | |
| 2011/0313252 A1 | 12/2011 | Lin | |
| 2012/0034573 A1 | 2/2012 | Erdmann | |
| 2015/0365571 A1 * | 12/2015 | Wada | G02B 23/26 |
| | | | 348/374 |
| 2015/0378144 A1 | 12/2015 | Handte | |

(Continued)

FOREIGN PATENT DOCUMENTS

| CN | 106061350 A | 10/2016 |
| CN | 112107283 A | 12/2020 |

(Continued)

*Primary Examiner* — Aaron B Fairchild
(74) *Attorney, Agent, or Firm* — Winston Hsu

(57) ABSTRACT

An endoscopic image capturing assembly is provided and includes a holder, an image sensing device, a conducting track, a cable and a lens set. The holder includes a first surface and a second surface perpendicular to the first surface. The image sensing device is mounted on the first surface and includes an electrical connecting component. The conducting track is formed from the first surface to the second surface of the holder and electrically connected to the electrical connecting component. The cable is mounted on the second surface. A terminal of the cable is electrically connected to the electrical connecting component of the image sensing device by the conducting track. The lens set is assembled with the image sensing device. An optical axis of the lens set is parallel to an extending direction of the cable. Furthermore, a related endoscopic device is provided.

19 Claims, 17 Drawing Sheets

(56) References Cited

U.S. PATENT DOCUMENTS

| | | | |
|---|---|---|---|
| 2018/0242826 A1 | 8/2018 | Shimohata | |
| 2018/0338674 A1* | 11/2018 | Kojima | A61B 1/00009 |
| 2019/0133423 A1* | 5/2019 | Birnkrant | A61B 1/04 |
| 2020/0069151 A1* | 3/2020 | Kobayashi | A61B 1/0676 |
| 2020/0221598 A1* | 7/2020 | Loo | H05K 1/184 |
| 2021/0249393 A1* | 8/2021 | Wu | H05K 1/189 |
| 2021/0345861 A1* | 11/2021 | Hosokai | A61B 1/00018 |
| 2021/0364778 A1 | 11/2021 | Loo | |

FOREIGN PATENT DOCUMENTS

| | | |
|---|---|---|
| EP | 3 155 957 A1 | 4/2017 |
| EP | 3 769 664 A1 | 1/2021 |
| JP | 2017-23234 | 2/2017 |
| TW | M576855 U | 4/2019 |
| TW | 202110386 A | 3/2021 |
| WO | 2018/230368 A1 | 12/2018 |
| WO | 2021/235510 A1 | 11/2021 |

* cited by examiner

ENDOSCOPIC IMAGE CAPTURING ASSEMBLY AND ENDOSCOPIC DEVICE THEREWITH

BACKGROUND OF THE INVENTION

1. Field of the Invention

The present invention relates to an image capturing assembly and an image capturing device therewith, and more specifically, to an endoscopic image capturing assembly with compact structure and small size and an endoscopic device therewith.

2. Description of the Prior Art

An endoscopy is a medical procedure in which an endoscope is inserted into a patient's body to allow a surgeon to inspect an interior of the patient's body. The endoscopy has gained broad acceptance because it only needs a small incision for insertion of the endoscope. However, since the conventional endoscope still has a bulky endoscopic image capturing assembly, a size of the incision cannot be further reduced in order for insertion of the endoscope with such a bulky endoscopic image capturing assembly. Therefore, an improvement is required.

SUMMARY OF THE INVENTION

It is an objective of the present invention to provide an endoscopic image capturing assembly with compact structure and small size and an endoscopic device therewith for solving the aforementioned problem.

In order to achieve the aforementioned objective, the present invention discloses an endoscopic image capturing assembly. The endoscopic image capturing assembly includes a holder, an image sensing device, a conducting track, a cable and a lens set. The holder includes a first surface and a second surface perpendicular to the first surface. The image sensing device is mounted on the first surface and includes an electrical connecting component. The conducting track is formed from the first surface to the second surface of the holder and electrically connected to the electrical connecting component. The cable is mounted on the second surface. A terminal of the cable is electrically connected to the conducting track, so that the terminal of the cable is electrically connected to the electrical connecting component by the conducting track. The lens set is assembled with the image sensing device. An optical axis of the lens set is parallel to an extending direction of the cable.

In order to achieve the aforementioned objective, the present invention further discloses an endoscopic device. The endoscopic device includes the aforementioned endoscopic image capturing assembly and an insertion tube connected to the endoscopic image capturing assembly.

In summary, the present invention utilizes the conducting track formed from the first surface of the holder to the second surface of the holder substantially perpendicular to the first surface of the holder, for being electrically connected to the electrical connecting component of the image sensing device mounted on the first surface of the holder and the terminal of the cable mounted on the second surface of the holder, so that the electrical connecting component of the image sensing device can be electrically connected to the terminal of the cable by the conducting track. The aforementioned configuration of the present invention has space-saving arrangement. Therefore, the present invention has advantages of compact structure and small size.

These and other objectives of the present invention will no doubt become obvious to those of ordinary skill in the art after reading the following detailed description of the preferred embodiment that is illustrated in the various figures and drawings.

DETAILED DESCRIPTION

In the following detailed description of the preferred embodiments, reference is made to the accompanying drawings which form a part hereof, and in which is shown by way of illustration specific embodiments in which the invention may be practiced. In this regard, directional terminology, such as "top", "bottom", "front", "back", etc., is used with reference to the orientation of the Figure (s) being described. The components of the present invention can be positioned in a number of different orientations. As such, the directional terminology is used for purposes of illustration and is in no way limiting. Accordingly, the drawings and descriptions will be regarded as illustrative in nature and not as restrictive. Also, the term "connect" is intended to mean either an indirect or direct electrical/mechanical connection. Thus, if a first device is connected to a second device, that connection may be through a direct electrical/mechanical connection, or through an indirect electrical/mechanical connection via other devices and connections.

Figure 1:
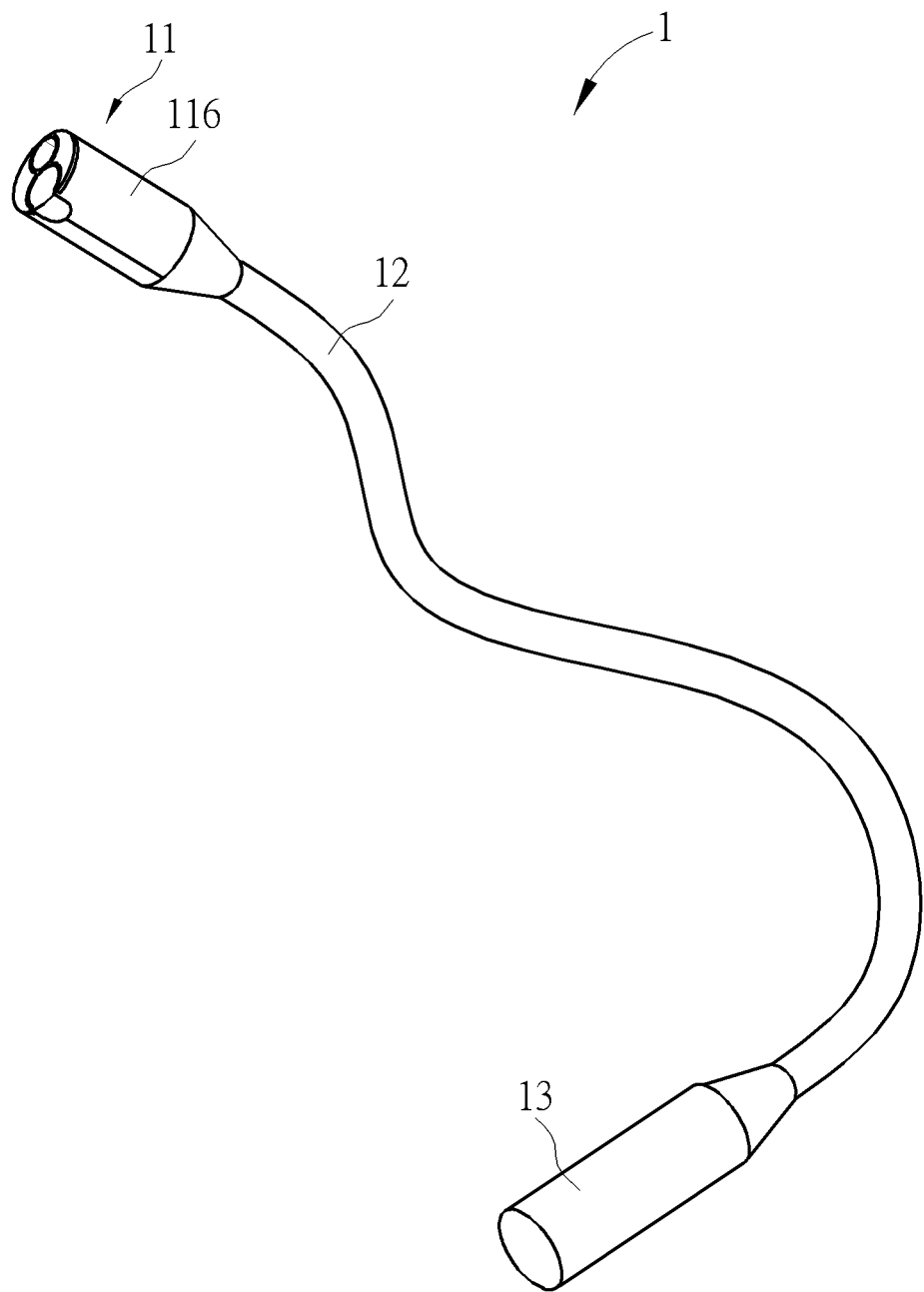
FIG. 1 is a schematic diagram of an endoscopic device according to a first embodiment of the present invention.

Please refer to FIG. 1. FIG. 1 is a schematic diagram of an endoscope 1 according to a first embodiment of the present invention. As shown in FIG. 1, the endoscopic device 1 includes an endoscopic image capturing assembly 11, an insertion tube 12 and a handle 13. The endoscopic image capturing assembly 11 is for capturing images of an interior of a patient's body, such as an internal organ or tissue of a patient's body. The handle 13 is for hand-holding and can be provided with a control console for at least controlling the endoscopic image capturing assembly 11. The insertion tube 12 is connected between the endoscopic image capturing assembly 11 and the handle 13. The insertion tube 12 is configured to be inserted into an interior lumen of the patient, so that the endoscopic image capturing assembly 11 can capture the images of the internal organ or tissue of the patient. Preferably, the insertion tube 12 can be made of flexible material. However, the present invention is not limited thereto. For example, in another embodiment, the insertion tube can be made of rigid material.

Figure 2:
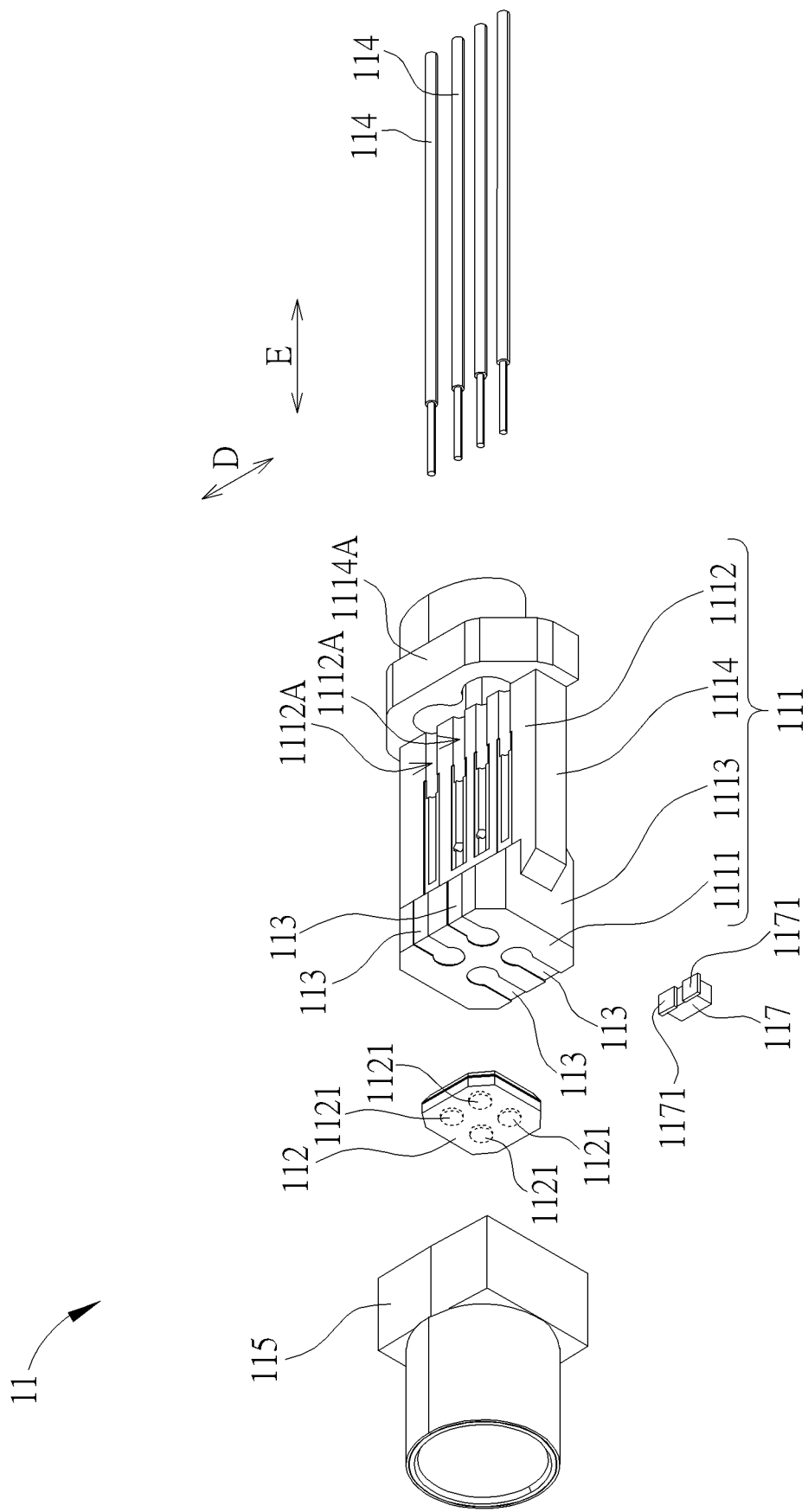
FIG. 2 is a partial exploded diagram of an endoscopic image capturing assembly according to the first embodiment of the present invention.
Figure 3:
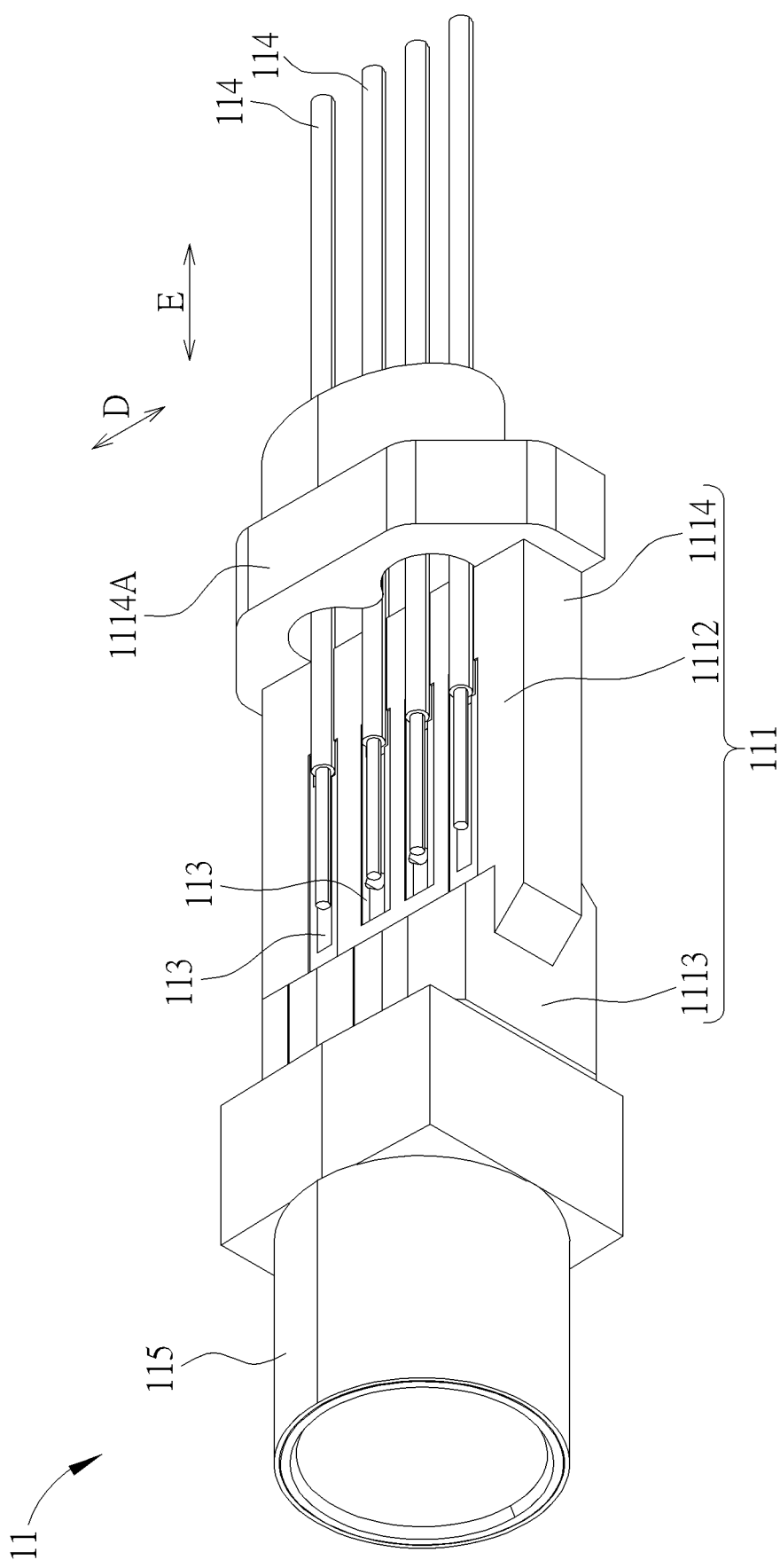
FIG. 3 and FIG. 4 are partial diagrams of the endoscopic image capturing assembly at different views according to the first embodiment of the present invention.
Figure 4:
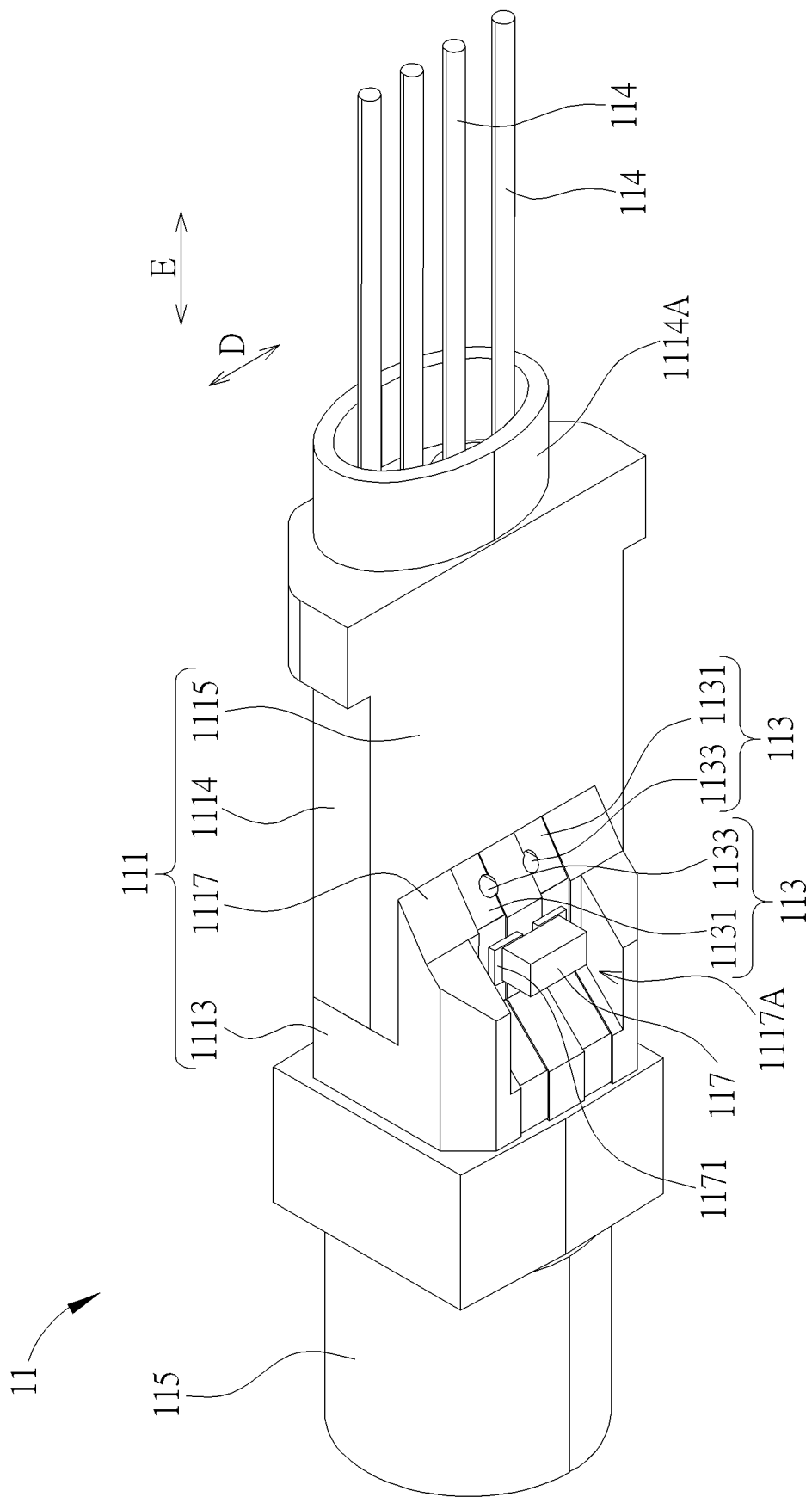

Please refer to FIG. 1 to FIG. 4. FIG. 2 is a partial exploded diagram of the endoscopic image capturing assembly 11 according to the first embodiment of the present invention. FIG. 3 and FIG. 4 are exploded diagrams of the endoscopic image capturing assembly 11 at different views according to the first embodiment of the present invention. As shown in FIG. 1 to FIG. 4, the endoscopic image capturing assembly 11 is located at a distal end of the insertion tube 12 away from the handle 13, and the endoscopic image capturing assembly 11 includes a holder 111, an image sensing device 112, four conducting tracks 113, four cables 114, a lens set 115 and a housing 116 for at least partially accommodating the holder 111, the image sensing device 112, the four conducting tracks 113 and the lens set 115.

Preferably, at least one of the conducting tracks 113 can be formed on the holder 111 by laser direct structuring technology.

Figure 5:
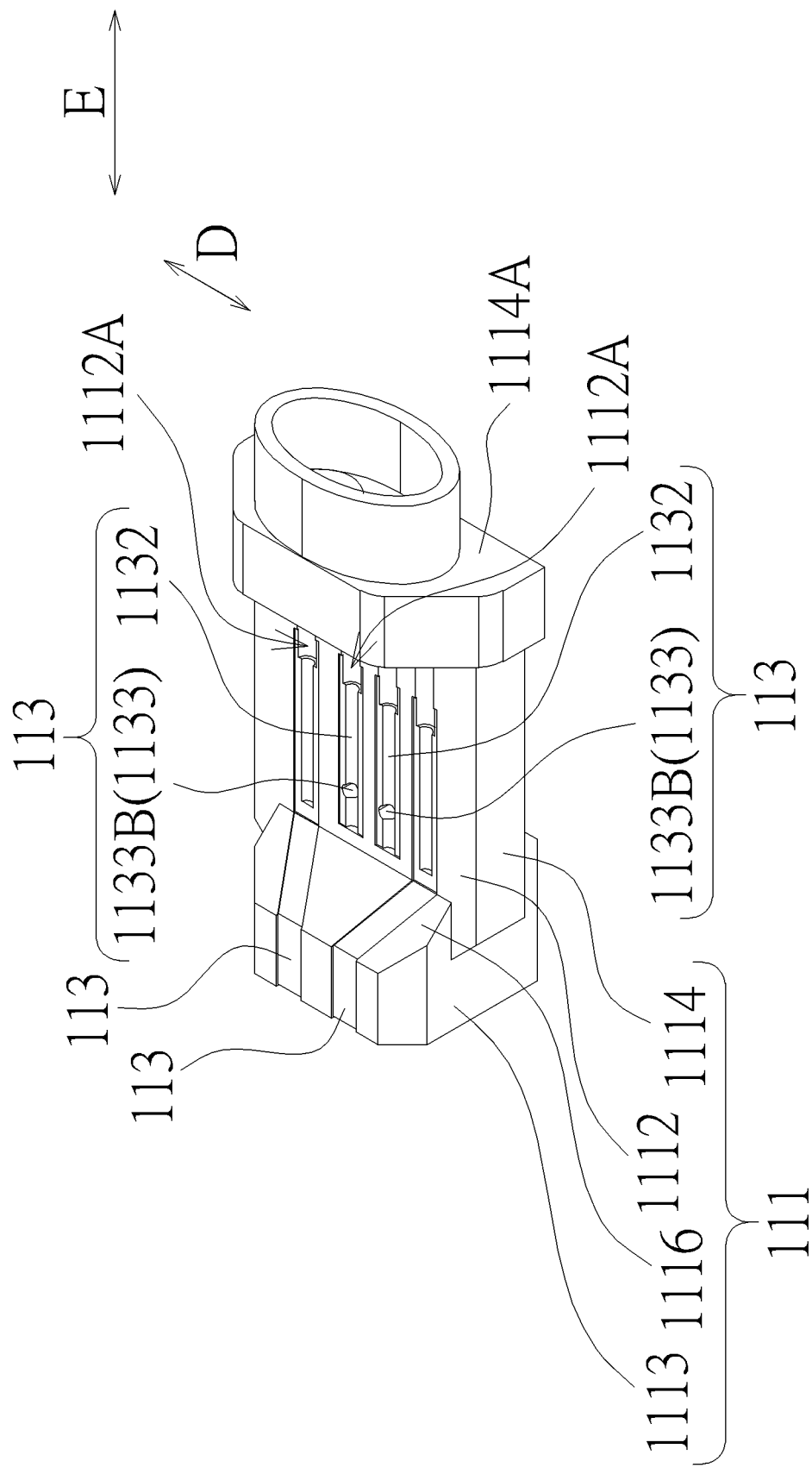
FIG. 5 is a diagram of a holder according to the first embodiment of the present invention.
Figure 6:
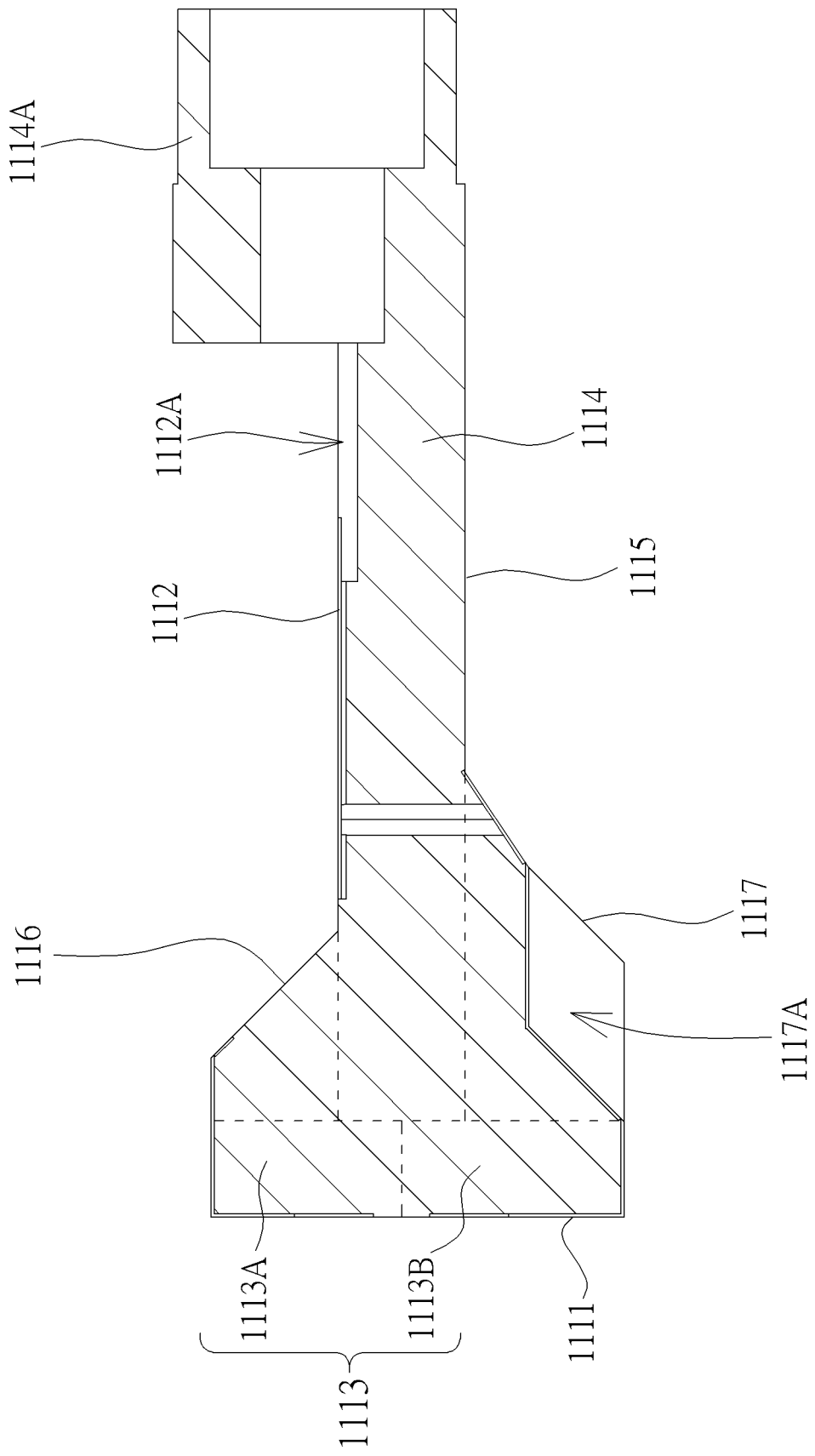
FIG. 6 is a sectional diagram of the holder according to the first embodiment of the present invention.

Please refer to FIG. 1 to FIG. 6. FIG. 5 is a diagram of the holder 111 according to the first embodiment of the present invention. FIG. 6 is a sectional diagram of the holder 111 according to the first embodiment of the present invention. As shown in FIG. 1 to FIG. 6, the holder 111 includes a first surface 1111 and a second surface 1112 substantially perpendicular to the first surface 1111.

The image sensing device 112 is mounted on the first surface 1111 and includes four electrical connecting components 1121. The four conducting tracks 113 are formed from the first surface 1111 to the second surface 1112 of the holder 111, i.e., a portion of each of the conducting tracks 113 is located on the first surface 1111, and another portion of each of the conducting tracks 113 is located on the second surface 1112. The four conducting tracks 113 are electrically connected to the four electrical connecting components 1121 respectively. The four cables 114 pass through the insertion tube 12 and are mounted on the second surface 1112. A terminal of each of the cables 114 is electrically connected to the corresponding conducting track 113, so that the terminal of each of the cables 114 is electrically connected to the corresponding electrical connecting component 1121 by the corresponding conducting track 113. Another terminal of each of the cables 114 is electrically connected to a circuit board of the control console of the handle 13, which is not shown in the figures, so that each of the cables 114 can provide power and/or signal transmission between the conducting track 113 and the circuit board of the control console of the handle 13. The lens set 115 is assembled with the image sensing device 112. An optical axis of the lens set 115 is substantially parallel to an extending direction E of each of the cables 114.

Specifically, in this embodiment, the image sensing device 112 can be a CMOS sensor and can be mounted on the first surface 1111 by surface mount technology, so as to affix and electrically connect each of the electrical connecting components 1121 onto a portion of the corresponding conducting track 113 located on the first surface 1111. The lens set 115 can be a fixed focal length lens set or a zoom lens set configured to zoom in or zoom out a view of the image sensing device 112. An engaging recess can be formed on the lens set 115, and the lens set 115 can be assembled with the image sensing device 112 by an engagement of the engaging recess and the image sensing device 112. The terminal of each of the cables 114 can be a conducting part of each of the cables 114 and electrically connected to the corresponding conducting track 113 by soldering. However, the present invention is not limited to this embodiment.

Besides, as shown in FIG. 2 to FIG. 6, the holder 111 further includes a first body 1113, a second body 1114, a third surface 1115, a transition portion 1116 and a transformation portion 1117. The first body 1113 is connected to the second body 1114. The first body 1113 is located between the image sensing device 112 and the second body 1114. The first surface 1111 is formed on the first body 1113. The second surface 1112 and the third surface 1115 are formed on the second body 1114 and located opposite to each other. The third surface 1115 is parallel to the second surface 1112. The second surface 1112 and the third surface 1115 can be an upper surface and a lower surface of the second body 1114, and a normal direction of the second surface 1112 and a normal direction of the third surface 1115 can be substantially perpendicular to the extending direction E. The first surface 1111 can be a front end surface of the first body 1113, and a normal direction of the first surface 1111 can be substantially parallel to the extending direction E. The four cables 114 are arranged in at intervals along a direction D substantially perpendicular to the extending direction E and the normal direction of the second surface 1112.

A projection area of the first body 1113 along the extending direction E is greater than a projection area of the second body 1114 along the extending direction E, wherein the projection area of the first body 1113 along the extending direction E can have a smaller dimension in the direction D than the projection area of the second body 1114 along the extending direction E, and the projection area of the first body 1113 along the extending direction E can have a greater dimension in the normal direction of the second surface 1112 than the projection area of the second body 1114 along the extending direction E. The first body 1113 includes a first part 1113A adjacent to the second surface 1112 and a second part 1113B adjacent to the third surface 1115. The transition portion 1116 is connected to the first part 1113A of the first body 1113 and the second body 1114 and formed between the first body 1113 and the second surface 1112, and the transformation portion 1117 is connected to the second part 1113B of the first body 1113 opposite to the first part 1113A of the first body 1113 and the second body 1114 and formed between the first body 1113 and the third surface 1115.

Specifically, in this embodiment, a cross section of the transition portion 1116 can be formed in a trapezoid shape substantially, and a cross section of the transformation portion 1117 can be formed in a shape of two stacked trapezoids substantially. However, the present invention is not limited thereto. For example, in another embodiment, the cross section of the transition portion or the transformation portion can be formed in shape of a triangle, a trapezoid, a rectangle, a circular sector, or a combination thereof.

Furthermore, each of two of the conducting tracks 113 is routed from the first surface 1111 to the second surface 1112 via at least an outer surface of the transition portion 1116. Each of the other two of the conducting tracks 113 includes a first track component 1131, a second track component 1132 and a via component 1133. The first track component 1131 is routed from the first surface 1111 to the transformation portion 1117 via at least an outer surface of the transformation portion 1117. The second track component 1132 is disposed on the second surface 1112.

The via component 1133 includes a first conducting structure 1133A and a second conducting structure 1133B. The first conducting structure 1133A is adjacent to the transformation portion 1117 and electrically connected to the first track component 1131. The second conducting structure 1133B is adjacent to the second surface 1112 and electrically connected to the first conducting structure 1133A and the second track component 1132.

Specifically, in this embodiment, the via component 1133 can be a plated through hole structure penetrating the second body 1114 and the transformation portion 1117, and the first conducting structure 1133A and the second conducting structure 1133B can be two end portions of the plated through hole structure adjacent to the transformation portion 1117 and the second surface 1112 respectively and electrically connected by a plated inner wall portion of the plated through hole structure, which is not shown in the figures.

However, the present invention is not limited to this embodiment. For example, in another embodiment, the first track component is routed from the first surface to the third surface, and the first conducting structure is adjacent to on the third surface and electrically connected to the first track component. Alternatively, in another embodiment, the first track component is routed from the first surface to the transformation portion, and the via component can be a combination of two blind hole structures and an inner conductive layer electrically connected to the two blind hole structures, wherein the first conducting structure and the second conducting structure can be an end portion of one of the blind hole structures adjacent to the transformation portion and an end portion of the other one of the blind hole structures adjacent to the second surface respectively. Alternatively, in another embodiment, the first track component is routed from the first surface to the third surface, and the via component can be a combination of two blind hole structures and an inner conductive layer electrically connected to the two blind hole structures, wherein the first conducting structure and the second conducting structure can be an end portion of one of the blind hole structures adjacent to the third surface and an end portion of the other one of the blind hole structures adjacent to the second surface respectively.

As shown in FIG. 2, FIG. 3, FIG. 5 and FIG. 6, in this embodiment, in order to facilitate a soldering process of an electrical connection between each of the conducting tracks 113 and the corresponding cable 114 and make an overall structure more compact, the endoscopic image capturing assembly 11 can further include a sleeve structure 1114A connected to an end of the second body 1114 away from the first body 1113, and four grooves 1112A can be formed on the second surface 1112. The four cables 114 can pass through the sleeve structure 1114A, so as to be mounted on the second surface 1112, and each of the grooves 1112A can at least partially accommodate the corresponding conducting track 113 and the corresponding cable 114.

Specifically, a portion of each of the two of the conducting tracks 113 routed from the first surface 1111 to the second surface 1112 via at least the outer surface of the transition portion 1116 is accommodated inside the corresponding groove 1112A. Each of the second components 1132 of the other two of the conducting tracks 113 is accommodated inside the corresponding groove 1112A. The terminal of each of the cables 1114 is accommodated inside the corresponding groove 1112A.

However, the present invention is not limited to this embodiment. For example, there can be no groove formed on the second surface.

In addition, as shown in FIG. 4, the endoscopic image capturing assembly 11 further includes a passive electronic component 117, e.g., a capacitor or a resistor, disposed on the holder 111 and electrically connected to the two corresponding conducting tracks 113.

Specifically, in this embodiment, in order to make the overall structure more compact, an accommodating notch 1117A is formed on the transformation portion 1117. The first track component 1131 of each of the two corresponding conducting tracks 113 is routed along a wall of the accommodating notch 1117A, and the passive electronic component 117 is at least partially disposed in the accommodating notch 1117A and electrically connected to the two corresponding conducting tracks 113, e.g., by two soldering structures 1171.

However, the present invention is not limited to this embodiment. For example, in another embodiment, there can be no accommodating notch formed on the transformation portion for at least partially accommodating the passive electronic component.

Alternatively, in another embodiment, the passive electronic component can be omitted. Alternatively, in another embodiment, the passive electronic component can be disposed on the third surface and electrically connected to the two corresponding conducting tracks by two bonding wires.

The aforementioned configuration of the first embodiment of the present invention has a space-saving arrangement. Therefore, the present invention has advantages of compact structure and small size.

Figure 7:
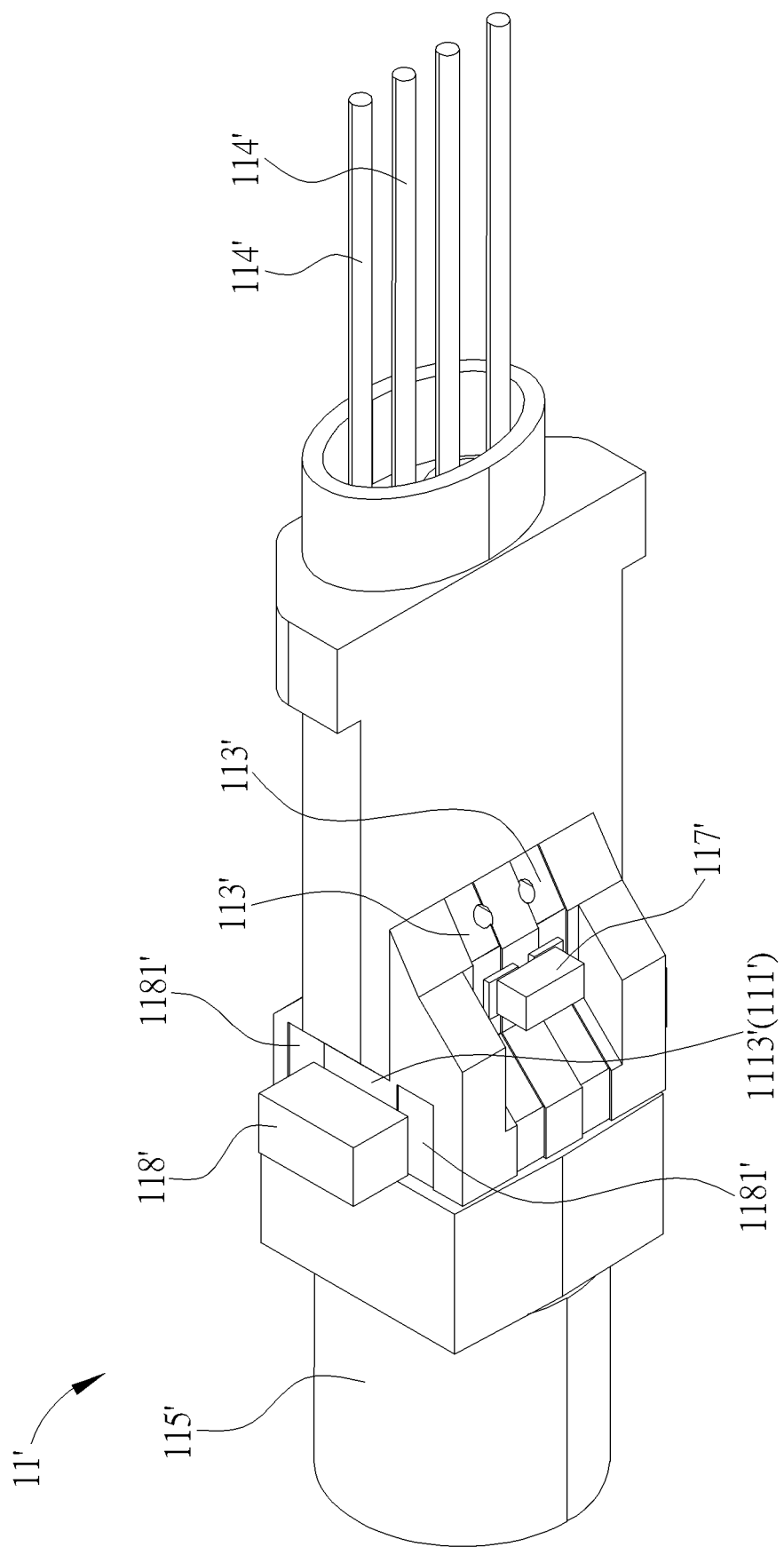
FIG. 7 is a partial diagram of an endoscopic image capturing assembly according to a second embodiment of the present invention.
Figure 8:
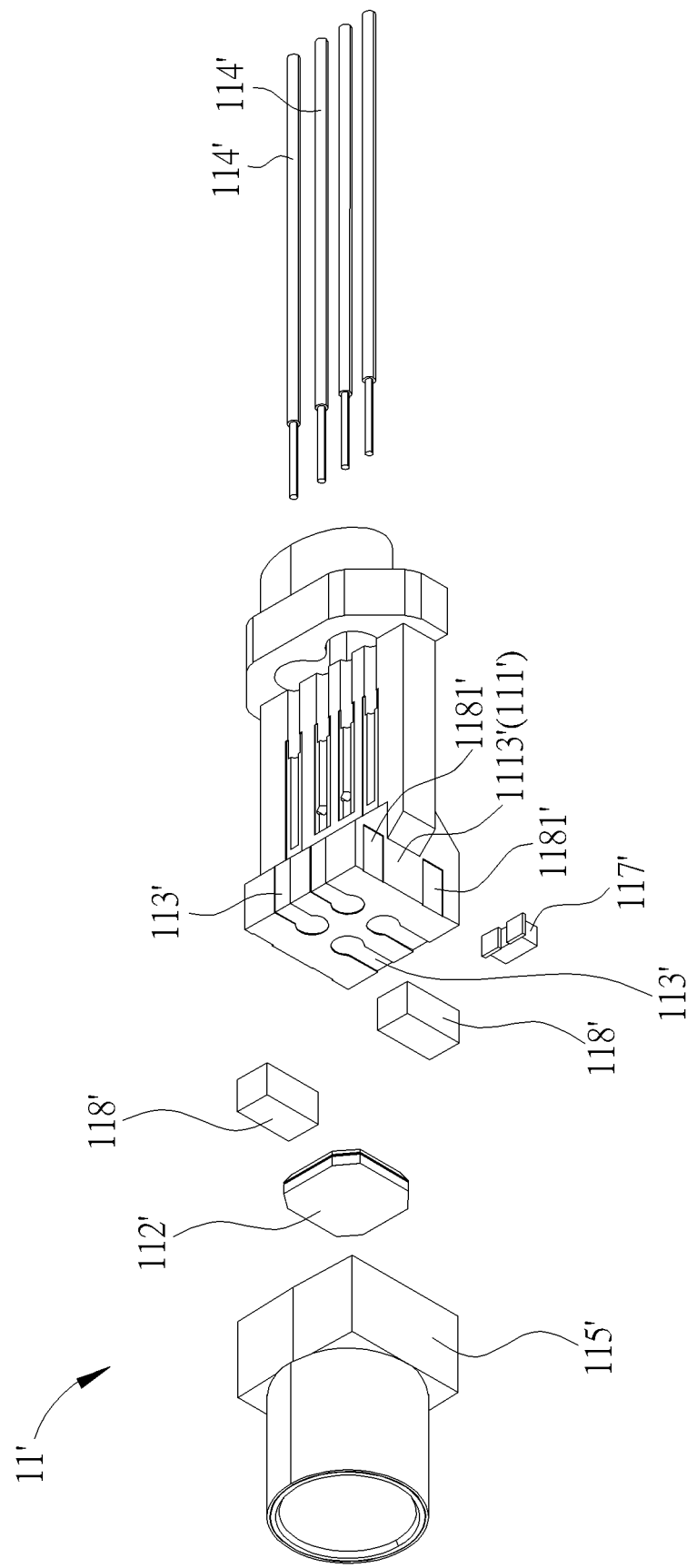
FIG. 8 is a partial exploded diagram of the endoscopic image capturing assembly according to the second embodiment of the present invention.

Please refer to FIG. 7 to FIG. 8. FIG. 7 is a partial diagram of an endoscopic image capturing assembly 11' according to a second embodiment of the present invention. FIG. 8 is a partial exploded diagram of the endoscopic image capturing assembly 11' according to the second embodiment of the present invention. The endoscopic image capturing assembly 11' includes a holder 111', an image sensing device 112', four conducting tracks 113', four cables 114', a lens set 115', a housing which is not shown in the figures, and a passive electronic component 117'.

As shown in FIG. 7 to FIG. 8, different from the first embodiment, the endoscopic image capturing assembly 11' further includes two light emitting components 118' respectively disposed on two lateral sides of the holder 111'.

Specifically, in this embodiment, the two light emitting components 118' can be respectively disposed on two lateral sides of a first body 1113' of the holder 111', and each of the light emitting components 118' can be affixed with and electrically connected to two corresponding contacts 1181' disposed on a corresponding lateral side of the first body 1113' of the holder 111' by soldering. The two light emitting components are configured to emit light for providing illumination. The light emitted from the light emitting component 118' can be guided outward a tip portion of the endoscopic image capturing assembly 11' by a corresponding light guiding component, which is not shown in the figures. Such configuration reduces a size of the tip portion of the endoscopic image capturing assembly 11'. Therefore, the endoscopic image capturing assembly 11' is space-saving. Furthermore, the endoscopic image capturing assembly 11' also has advantages of easy assembly and less part number. Other details of this embodiment are similar to the ones of the first embodiment. Detailed description is omitted herein for simplicity.

However, the present invention is not limited to this embodiment. For example, in another embodiment, there can be only one light emitting component disposed on one lateral side of the first surface, and the light emitting component can be electrically connected to the corresponding two contacts disposed on one lateral side of the first body of the holder by bonding wires. Alternatively, in another embodiment, the two corresponding contacts electrically connected to the light emitting component can extend to the second surface or the third surface and be electrically connected to a corresponding one of the cables.

Figure 9:
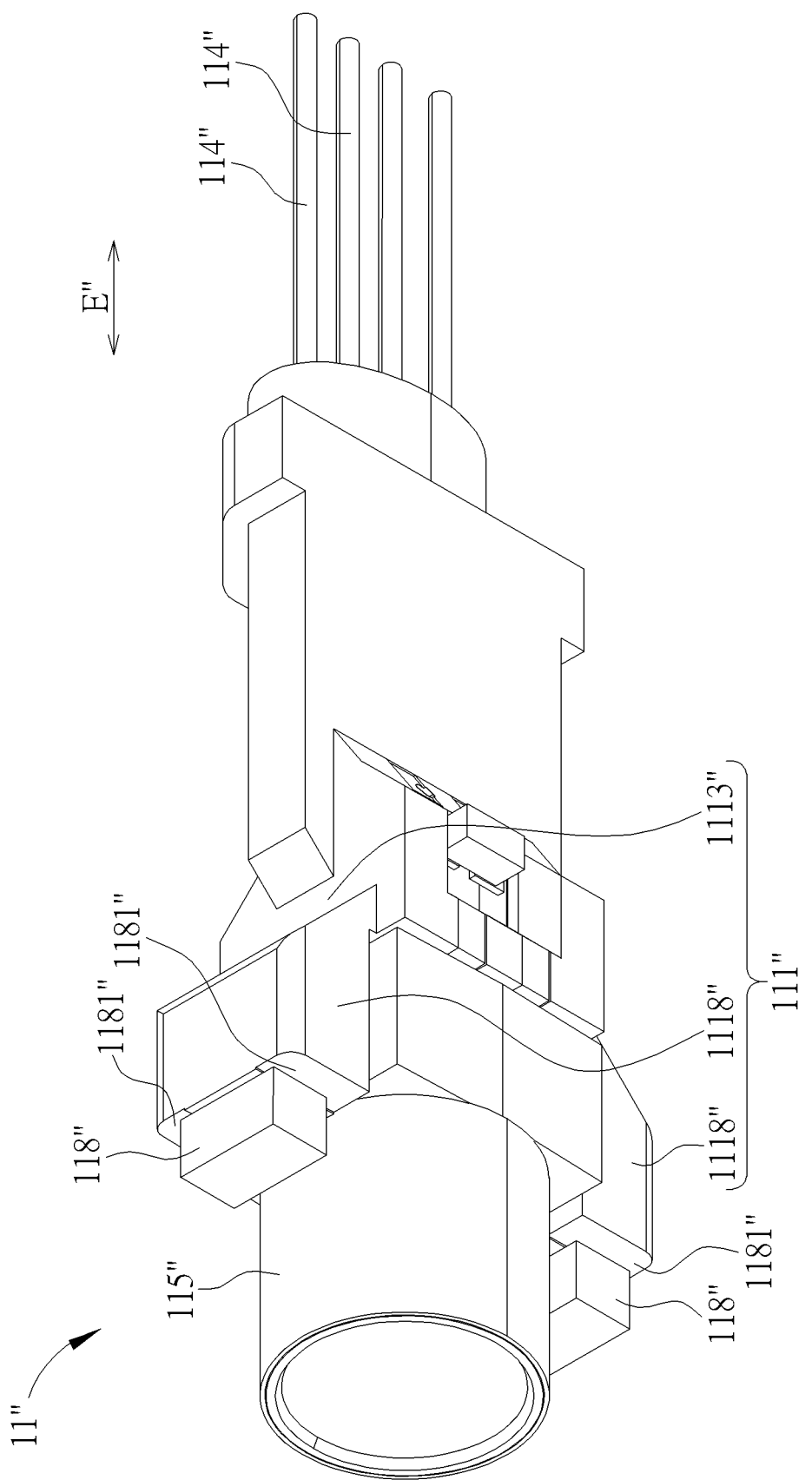
FIG. 9 is a partial diagram of an endoscopic image capturing assembly according to a third embodiment of the present invention.
Figure 10:
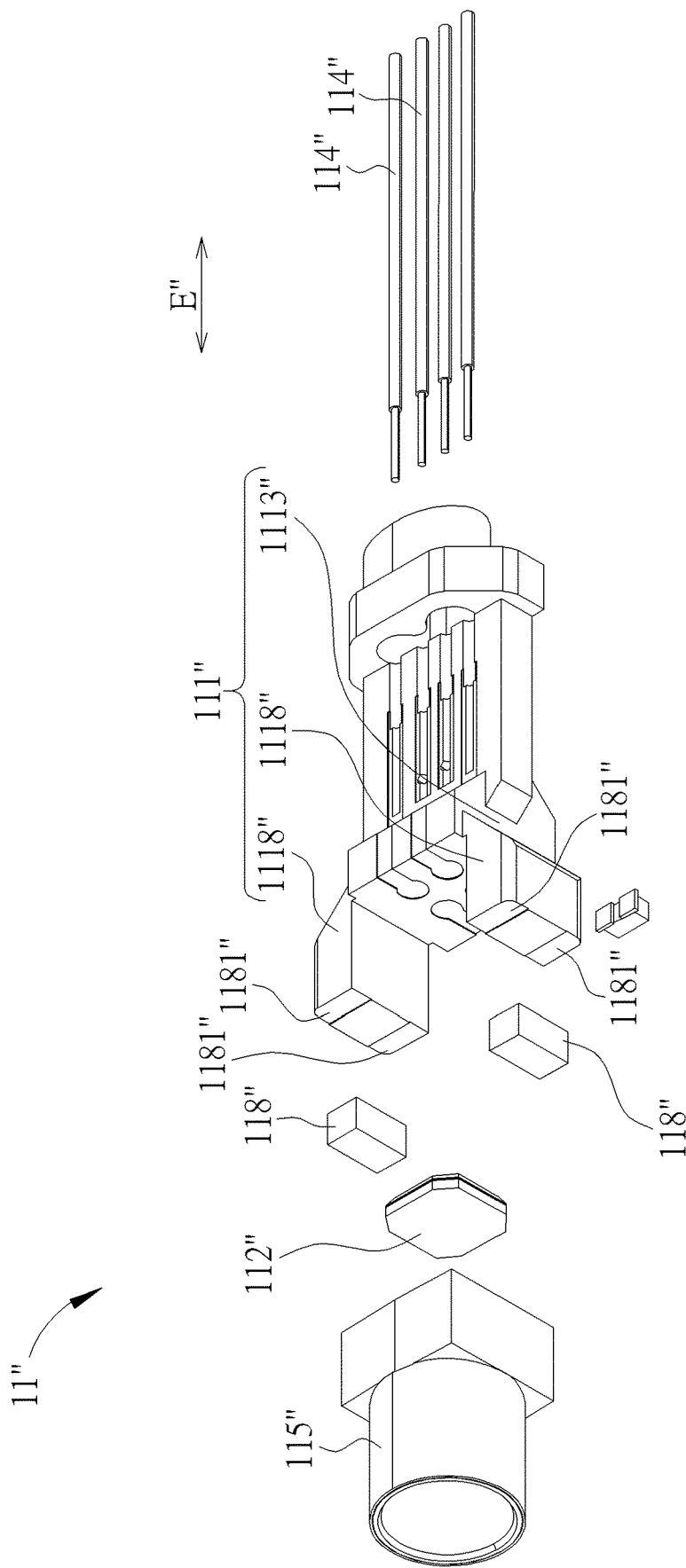
FIG. 10 is a partial exploded diagram of the endoscopic image capturing assembly according to the third embodiment of the present invention.

Please refer to FIG. 9 to FIG. 10. FIG. 9 is a partial diagram of an endoscopic image capturing assembly 11" according to a third embodiment of the present invention. FIG. 10 is a partial exploded diagram of the endoscopic image capturing assembly 11" according to the third embodiment of the present invention. The endoscopic image capturing assembly 11" includes a holder 111", an image sensing device 112", four conducting tracks 113", four cables 114", a lens set 115", a housing which is not shown in the figures, and a passive electronic component 117".

As shown in FIG. 9 to FIG. 10, different from the first embodiment, the endoscopic image capturing assembly 11" further includes two light emitting components 118" respectively disposed on two lateral sides of the holder 111".

Specifically, in this embodiment, the holder 111" includes two protruding bodies 1118" respectively connected to two lateral sides of a first body 1113" and extending along an extending direction E" of the cable 114". Each of the light emitting components 118" can be disposed on the corresponding protruding body 1118", and each of the light emitting components 118" is affixed with and electrically connected to two corresponding contacts disposed on the corresponding protruding body 1118" by soldering. Such configuration allows the light emitting components 118" to be adjacent to a tip portion of the endoscopic image capturing assembly 11" for preventing light emitted from the light emitting components 118" from being obstructed by the lens set 115", so as to provide better illumination. Besides, such configuration is adaptive to the light emitting component 118" with a different packaging structure from the light emitting component 118' of the second embodiment. In this embodiment, the light emitting component 118" can have pins located opposite to a light emitting surface of the light emitting component 118", and in the second embodiment, the light emitting component 118' can have pins located beside a light emitting surface of the light emitting component 118'. Other details of this embodiment are similar to the ones of the first embodiment. Detailed description is omitted herein for simplicity.

However, the present invention is not limited to this embodiment. For example, in another embodiment, there can be only one protruding body and one light emitting component disposed on the protruding body, and the light emitting component can be electrically connected to the two contacts disposed on the protruding body by bonding wires. Alternatively, in another embodiment, the two corresponding contacts electrically connected to the light emitting component can extend to the second surface or the third surface and be electrically connected to a corresponding one of the cables.

Figure 11:
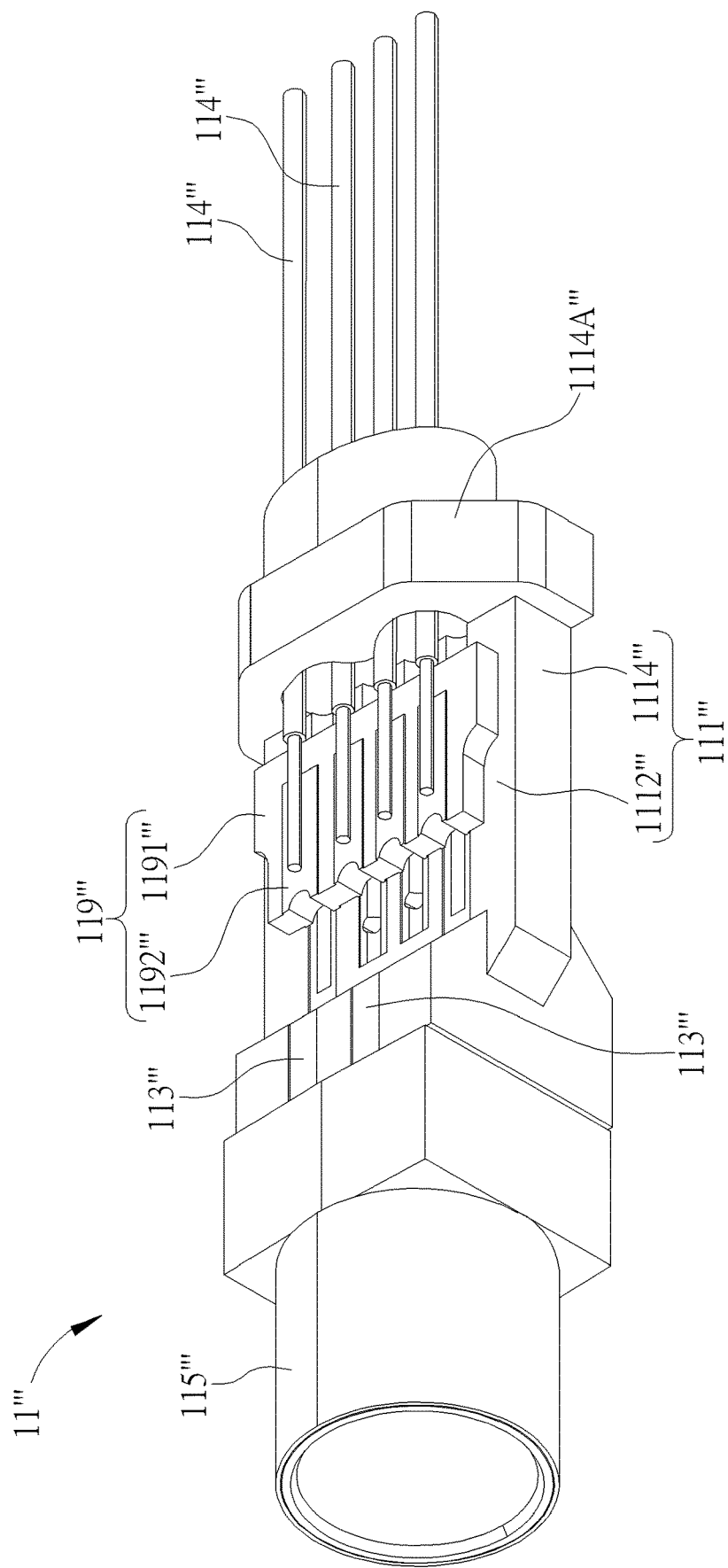
FIG. 11 is a partial diagram of an endoscopic image capturing assembly according to a fourth embodiment of the present invention.
Figure 12:
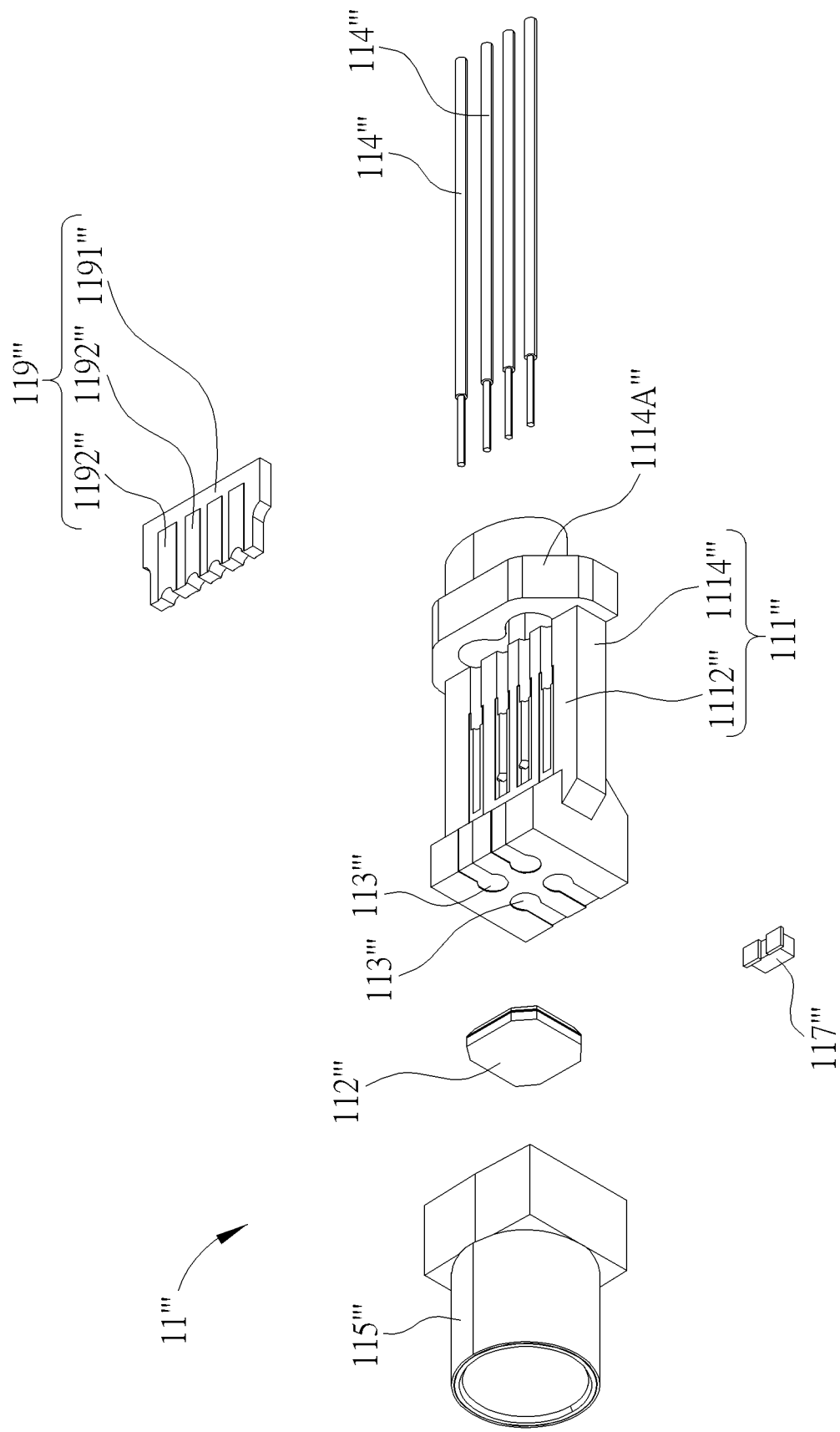
FIG. 12 and FIG. 13 are partial exploded diagrams of the endoscopic image capturing assembly at different views according to the fourth embodiment of the present invention.
Figure 13:
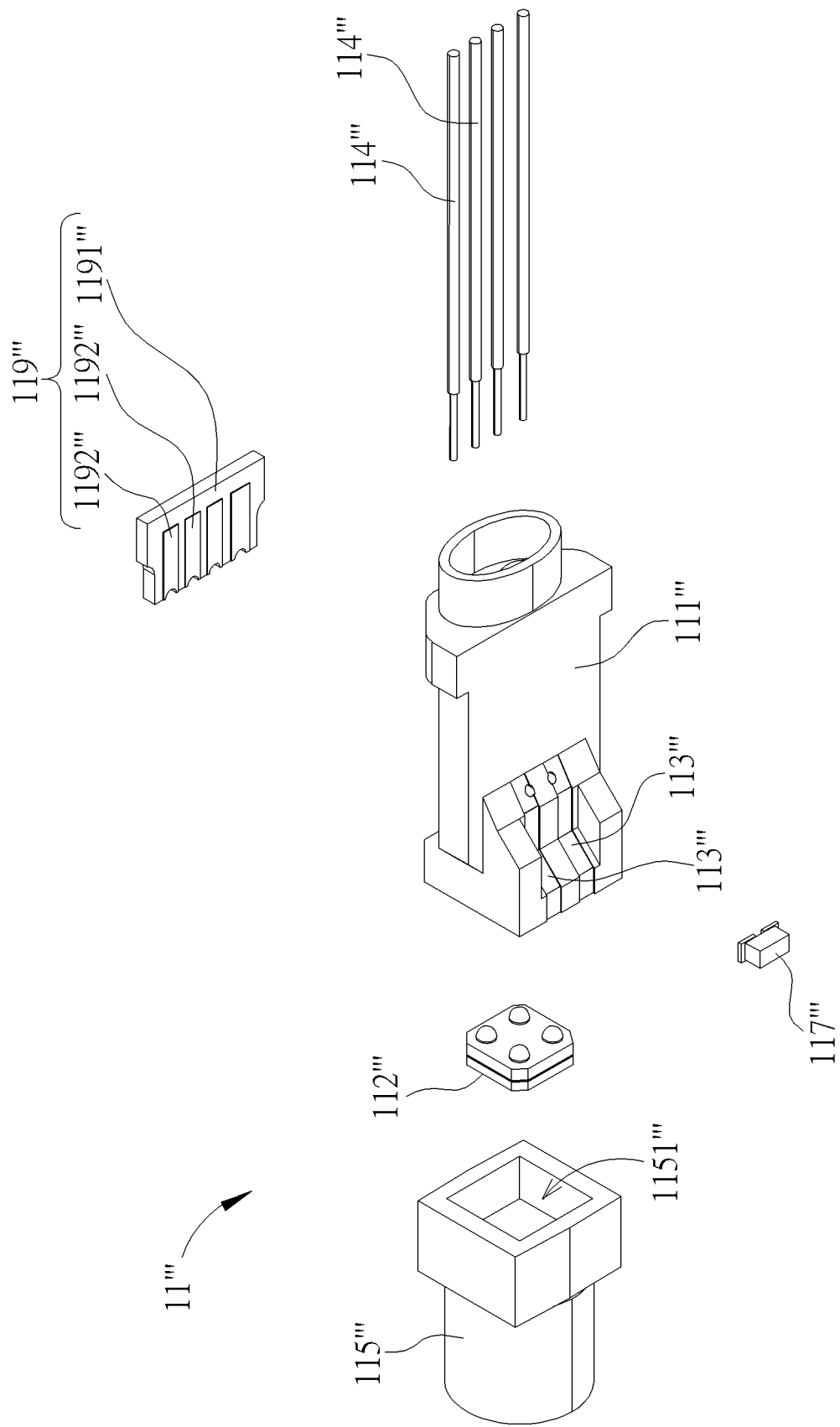

Please refer to FIG. 11 to FIG. 13. FIG. 11 is a partial diagram of an endoscopic image capturing assembly 11''' according to a fourth embodiment of the present invention. FIG. 12 and FIG. 13 are partial exploded diagrams of the endoscopic image capturing assembly 11''' at different views according to the fourth embodiment of the present invention. The endoscopic image capturing assembly 11''' includes a holder 111', an image sensing device 112''', four conducting tracks 113''', four cables 114''', a lens set 115''', a housing which is not shown in the figures, and a passive electronic component 117'''. As shown in FIG. 13, similar to the first embodiment, an engaging recess 1151''' is formed on the lens set 115''' for engaging with the image sensing device 112'''.

As shown in FIG. 11 to FIG. 13, different from the first embodiment, the endoscopic image capturing assembly 11''' further includes an adaptor 119''' connected to the four cables 114''' and a second surface 1112''' of the holder 111''' and electrically connected between terminals of the four cables 114''' and the four conducting tracks 113'''.

Specifically, in this embodiment, the adaptor 119''' can be an adapting plate including a main body 1191''' disposed on the second surface 1112''' and four conducting components 1191''' disposed on the main body 1191'''. During assembly, an end of each of the cables 114''' can be affixed with and electrically connected to the corresponding conducting component 1191''' by soldering firstly, and then another end of each of the cables 114''' can pass through a sleeve structure 1114A'''. Afterwards, the main body 1191''' can be placed on the second surface 1112''' and can be connected to the second surface 1112''' by fastening components, adhesives, soldering or welding, and the four conducting components 1191''' can be affixed with and electrically connected to the four conducting tracks 113''' by soldering respectively, so as to electrically connect each of the cables 114''' to the corresponding conducting track 113''' by the corresponding conducting component 1191'''. Such configuration provides an easy assembly process even if the holder 111''' is too small to align the terminal of the cable 114''' with the conducting track 113'''. Other details of this embodiment are similar to the ones of the first embodiment. Detailed description is omitted herein for simplicity.

However, the assembly of the adaptor and the holder is not limited to this embodiment. For example, in another embodiment, the main body can be placed on the second surface and connected to the second surface by soldering connections of the conducting tracks and the conducting components.

Figure 14:
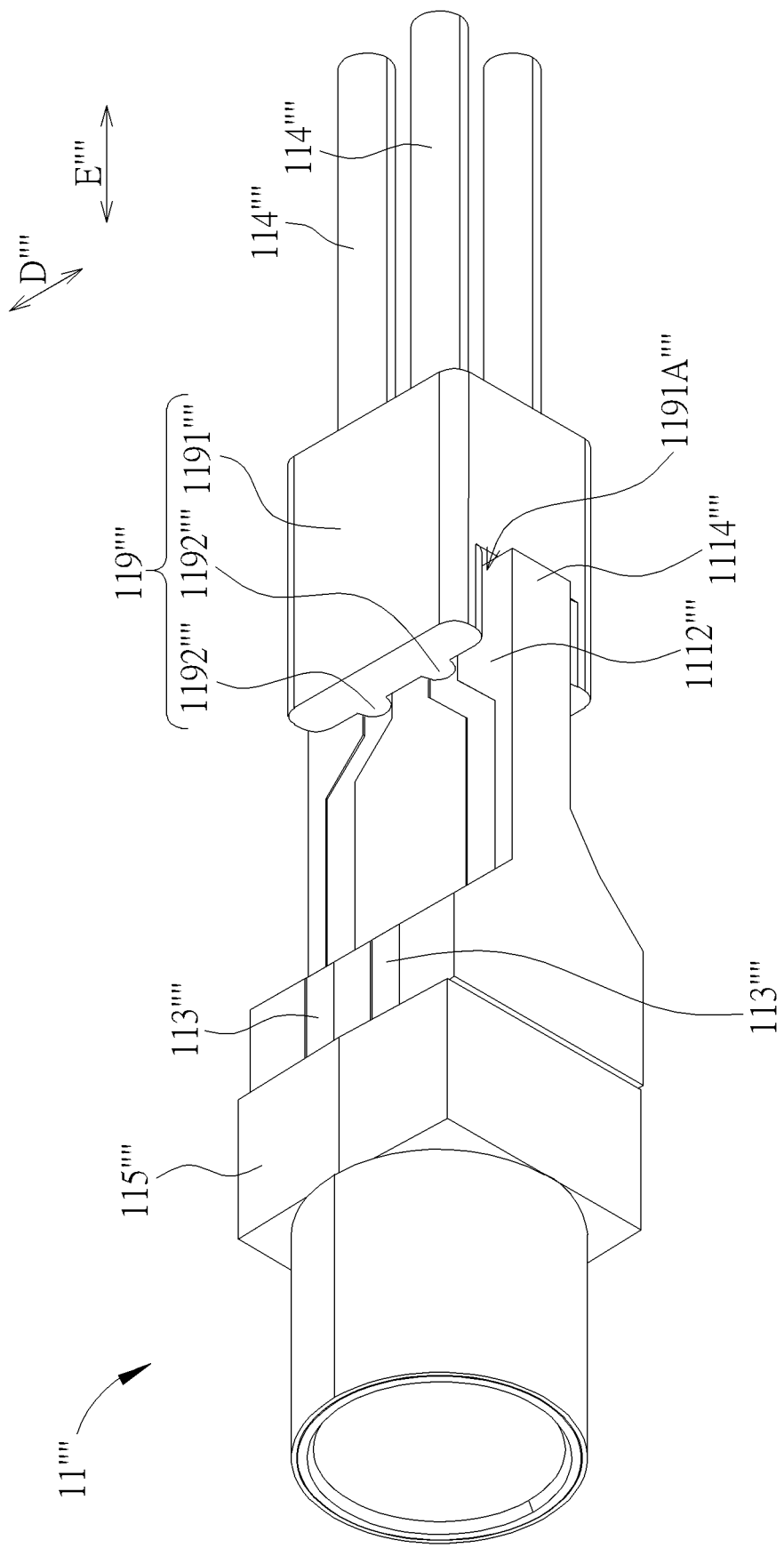
FIG. 14 is a partial diagram of an endoscopic image capturing assembly according to a fifth embodiment of the present invention.
Figure 15:
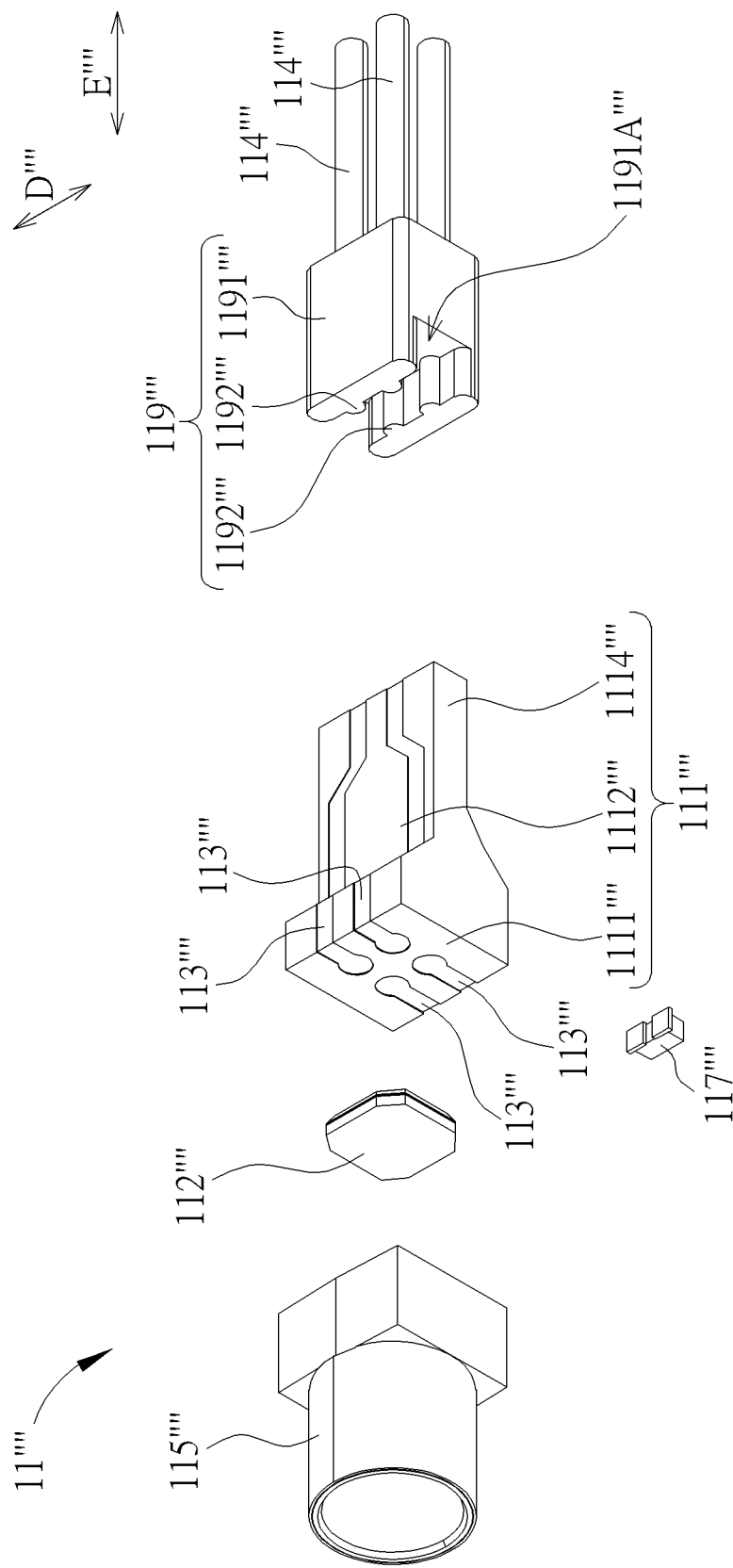
FIG. 15 to FIG. 17 are partial exploded diagrams of the endoscopic image capturing assembly at different views according to the fifth embodiment of the present invention.
Figure 16:
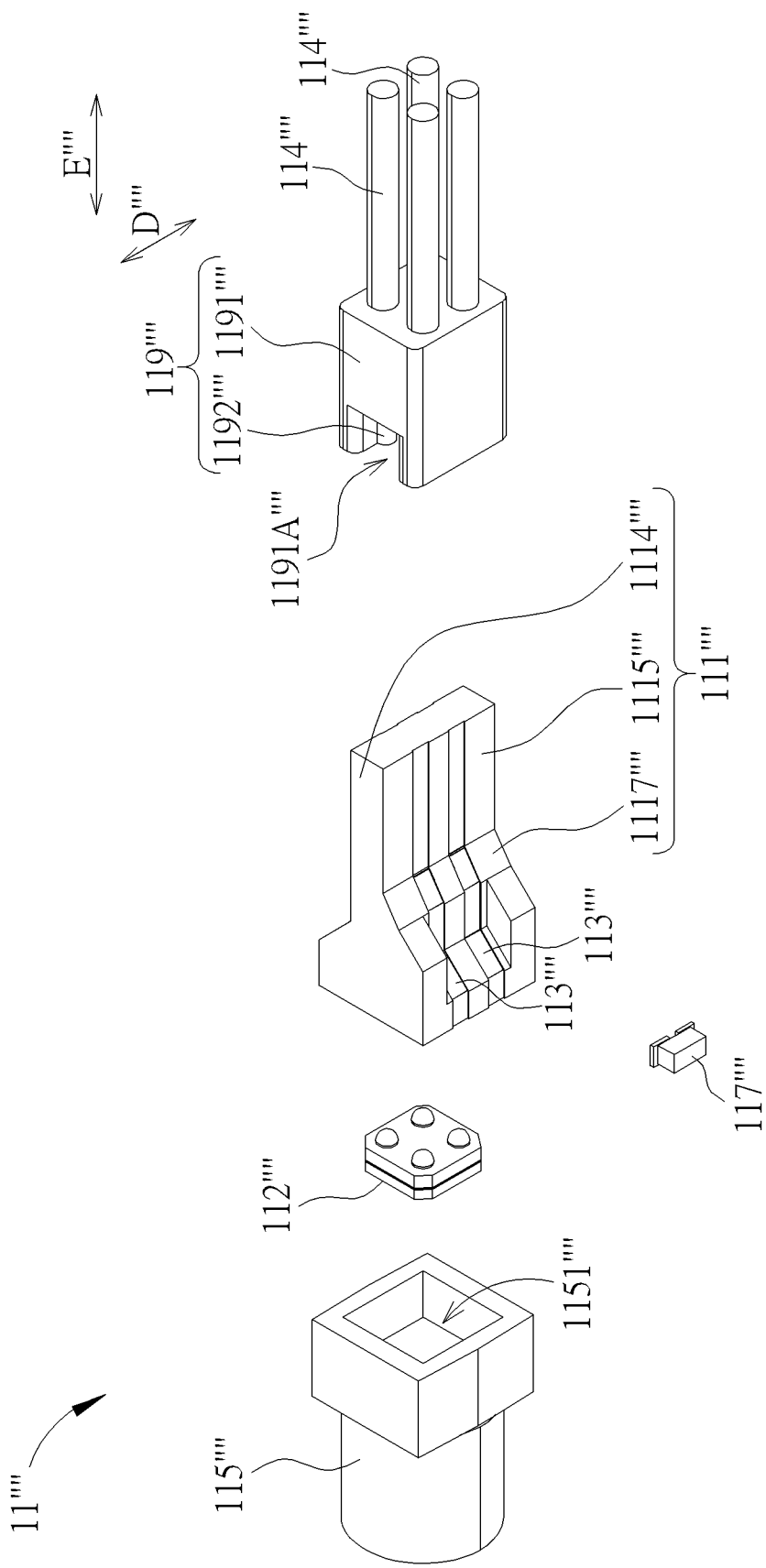
Figure 17:
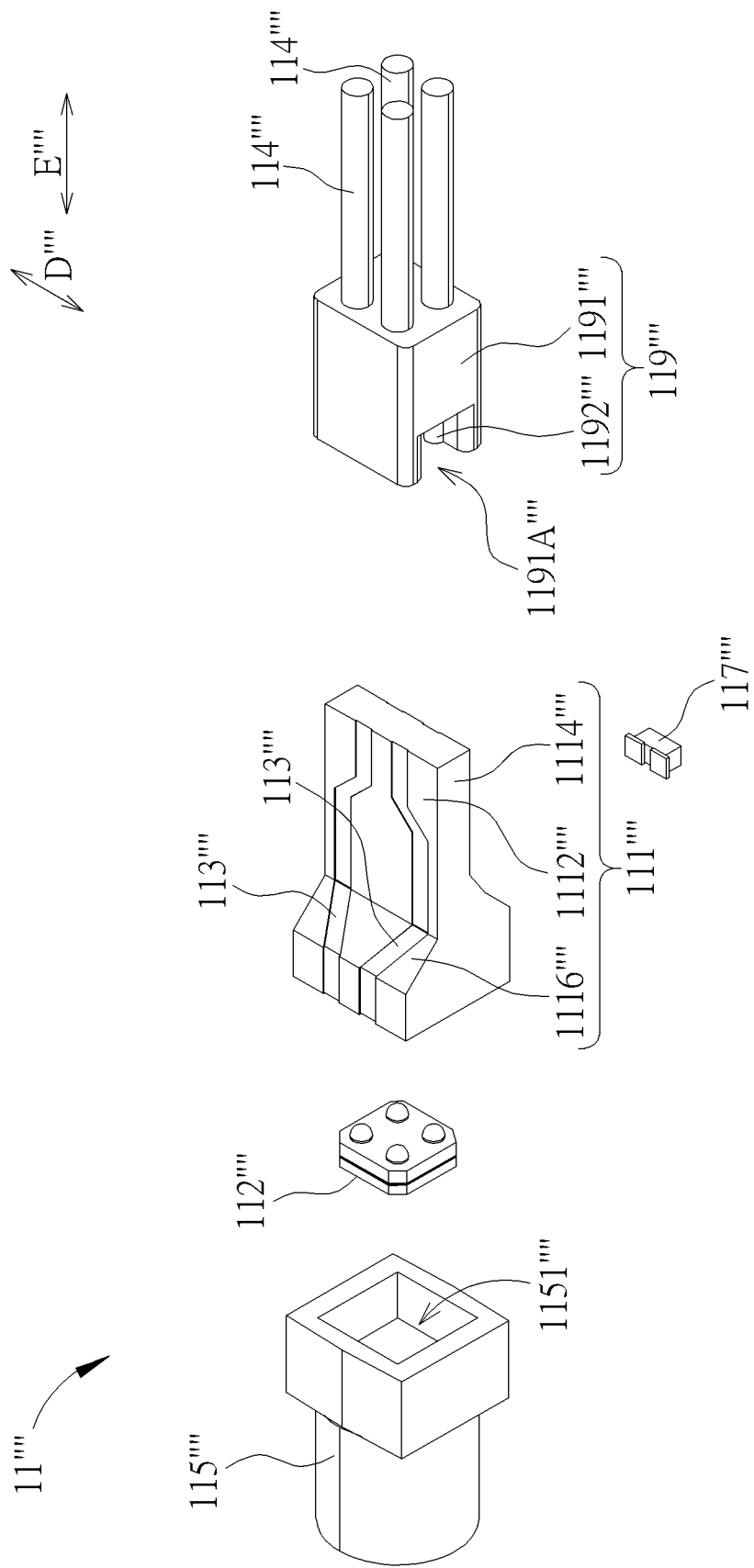

Please refer to FIG. 14 to FIG. 17. FIG. 14 is a partial diagram of an endoscopic image capturing assembly 11'''' according to a fifth embodiment of the present invention. FIG. 15 to FIG. 17 are partial exploded diagrams of the endoscopic image capturing assembly 11'''' at different views according to the fifth embodiment of the present invention. The endoscopic image capturing assembly 11'''' includes a holder 111'''', an image sensing device 112'''', four conducting tracks 113'''', four cables 114'''', a lens set 115'''', a housing which is not shown in the figures, and a passive electronic component 117''''. As shown in FIG. 16 and FIG. 17, similar to the first embodiment, an engaging recess 1151'''' is formed on the lens set 115'''' for engaging with the image sensing device 112''''.

As shown in FIG. 14 to FIG. 17, different from the first embodiment, a projection area of the first body 1113'''' along an extending direction E"" is greater than a projection area of the second body 1114"" along the extending direction E"", wherein the projection area of the first body 1113"" along the extending direction E and the projection area of the second body 1114"" along the extending direction E"" have equal dimensions in a direction D"", and the projection area of the first body 1113"" along the extending direction E"" can have a greater dimension in a normal direction of the second surface 1112"" than the projection area of the second body 1114"" along the extending direction E"".

Besides, the endoscopic image capturing assembly 11"" does not include the sleeve structure of the first embodiment, and the endoscopic image capturing assembly 11"" further includes an adaptor 119"" connected to the four cables 114"" and the holder 111"" and electrically connected between terminals of the four cables 114"" and the four conducting tracks 113"". Each of two of the conducting tracks 113"" is routed from a first surface 1111"" of the holder 111"" to a second surface 1112"" of the holder 111"" via at least an outer surface of a transition portion 1116"" of the holder 111"", and each of the other two of the conducting tracks 113"" is routed from the first surface 1111"" of the holder 111"" to a third surface 1115"" of the holder 111"" via at least an outer surface of a transformation portion 1117"" of the holder 111"". By the adaptor 119"", two of the cables 114"" can be mounted on the second surface 1112"" and electrically connected to the two corresponding conducting tracks 113"" disposed on the second surface 1112"", and the other two of the cables 114"" can be mounted on the third surface 1115"" and electrically connected to the two corresponding conducting tracks 113"" disposed on the third surface 1115"".

Specifically, in this embodiment, the adaptor 119"" can be an adapting connector including a main body 1191"" and four conducting components 1192"". An engaging notch 1191A"" is formed on the main body 1191"" for engaging with a second body 1114"" of the holder 111"". The four conducting components 1192"" are disposed on the main body 1191"". Two of the conducting components 1192"" are exposed to an upper wall of the engaging notch 1191A"" and are electrically connected to the two corresponding conducting tracks 113"" disposed on the second surface 1112"" by abutment. The other two of the conducting components 1192"" are exposed to a lower wall of the engaging notch 1191A"" and are electrically connected to the two corresponding conducting tracks 113"" disposed on the third surface 1115"" by abutment. Each of the cables 114"" is inserted into the main body 1191"" and electrically connected to the corresponding conducting component 1192"". The main body 1191"" can be made of resilient material and configured to be resiliently deformed to drive the four conducting components 1192"" to abut against the four conducting tracks 113"" firmly when the engaging notch 1191A"" engages with the second body 1114"". Other details of this embodiment are similar to the ones of the first embodiment. Detailed description is omitted herein for simplicity.

Furthermore, the present invention is not limited to the aforementioned embodiments. In another embodiment, there can be two electrical connecting components and two cables, wherein only one of the electrical connecting components is electrically connected to a corresponding one of the cables using one of the aforementioned configurations of the aforementioned embodiments, e.g., by the conducting track routed from the first surface to the second surface via at least the outer surface of the transition portion, or by the conducting track including the first track component, the second track component and the via component, and the other one of the electrical connecting components is electrically connected to the other one of the cables using another configuration.

In contrast to the prior art, the present invention utilizes the conducting track formed from the first surface of the holder to the second surface of the holder substantially perpendicular to the first surface of the holder, for being electrically connected to the electrical connecting component of the image sensing device mounted on the first surface of the holder and the terminal of the cable mounted on the second surface of the holder, so that the electrical connecting component of the image sensing device can be electrically connected to the terminal of the cable by the conducting track. The aforementioned configuration of the present invention has space-saving arrangement. Therefore, the present invention has advantages of compact structure and small size.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. An endoscopic image capturing assembly comprising:
   an image sensing device;
   a cable;
   a conducting track;
   a passive electronic component; and
   a holder comprising a first body, a second body, a transformation portion, a first surface, a second surface perpendicular to the first surface, a third surface and at least one continuous outer surface located between and connected to the first surface and the second surface;
   wherein the first surface is formed on the first body, the second surface and the third surface are formed on the second body and located opposite to each other, the transformation portion is formed between the first body and the third surface, and an accommodating notch is formed on the transformation portion;
   wherein the image sensing device is mounted on the first surface and comprises an electrical connecting component;
   wherein the conducting track is continuously formed from the first surface to the second surface of the holder along the at least one continuous outer surface of the holder and routed along a wall of the accommodating notch, two ends of the conducting track are respectively located on the first surface and the second surface of the holder, and the conducting track is electrically connected to the electrical connecting component;
   wherein the cable is mounted on the second surface, a terminal of the cable is electrically connected to the conducting track, so that the terminal of the cable is electrically connected to the electrical connecting component by the conducting track;
   wherein the passive electronic component is disposed on the holder, and the passive electronic component is at least partially disposed in the accommodating notch and electrically connected to the conducting track.

2. The endoscopic image capturing assembly of claim 1, wherein the holder further comprises a transition portion, the transition portion is connected to the first body and the second body, and the conducting track is routed from the first surface to the second surface via at least an outer surface of the transition portion.

3. The endoscopic image capturing assembly of claim 1, wherein the holder further comprises a transition portion, a projection area of the first body along an extending direction of the cable is greater than a projection area of the second body along the extending direction of the cable, the first body comprises a first part adjacent to the second surface and a second part adjacent to the third surface, the transition portion is connected to the first part of the first body and the second body, and the transformation portion is connected to the second part of the first body and the second body.

4. The endoscopic image capturing assembly of claim 1, wherein the conducting track comprises a first track component, a second track component and a via component, the first track component is routed from the first surface to one of the third surface and the transformation portion via at least an outer surface of the transformation portion, the second track component is disposed on the second surface, the via component comprises a first conducting structure and a second conducting structure, the first conducting structure is adjacent to the one of the third surface and the transformation portion, and the second conducting structure is adjacent to the second surface and electrically connected to the first conducting structure, the first track component and the second track component.

5. The endoscopic image capturing assembly of claim 1, wherein a groove is formed on the second surface and at least partially accommodates the conducting track and the cable.

6. The endoscopic image capturing assembly of claim 1, further comprising a light emitting component disposed on a lateral side of the holder, the holder further comprising a first body, and the light emitting component being disposed on a lateral side of the first body.

7. The endoscopic image capturing assembly of claim 1, further comprising a light emitting component disposed on a lateral side of the holder, the holder further comprising a first body and a protruding body connected to a lateral side of the first body and extending along an extending direction of the cable, and the light emitting component being disposed on the protruding body.

8. The endoscopic image capturing assembly of claim 1, further comprising an adaptor and a sleeve structure, the adaptor being disposed on the second surface, the cable passing through the sleeve structure and being connected to the adaptor, and the adaptor being electrically connected between the terminal of the cable and the conducting track.

9. The endoscopic image capturing assembly of claim 1, further comprising an adaptor disposed on the holder by abutting against the second surface and the third surface, the cable being connected to the adaptor, and the adaptor being electrically connected between the terminal of the cable and the conducting track.

10. The endoscopic image capturing assembly of claim 1, further comprising a lens set assembled with the image sensing device, and an optical axis of the lens set being parallel to an extending direction of the cable.

11. An endoscopic device comprising:
an endoscopic image capturing assembly comprising:
  an image sensing device comprising an electrical connecting component;
  a cable;
  a conducting track;
  a passive electronic component; and
  a holder comprising a first body, a second body, a transformation portion, a first surface, a second surface perpendicular to the first surface, a third surface and at least one continuous outer surface located between and connected to the first surface and the second surface;
  wherein the first surface is formed on the first body, the second surface and the third surface are formed on the second body and located opposite to each other, the transformation portion is formed between the first body and the third surface, and an accommodating notch is formed on the transformation portion;
  wherein the image sensing device is mounted on the first surface and comprises an electrical connecting component;
  wherein the conducting track is continuously formed from the first surface to the second surface of the holder along the at least one continuous outer surface of the holder and routed along a wall of the accommodating notch, two ends of the conducting track are respectively located on the first surface and the second surface of the holder, and the conducting track is electrically connected to the electrical connecting component;
  wherein the cable is mounted on the second surface, a terminal of the cable is electrically connected to the conducting track, so that the terminal of the cable is electrically connected to the electrical connecting component by the conducting track;
  wherein the passive electronic component is disposed on the holder, and the passive electronic component is at least partially disposed in the accommodating notch and electrically connected to the conducting track; and
an insertion tube connected to the endoscopic image capturing assembly.

12. The endoscopic device of claim 11, wherein the holder further comprises a transition portion, the first body comprises a first part adjacent to the second surface, the transition portion is connected to the first part of the first body and the second body, and the conducting track is routed from the first surface to the second surface via at least an outer surface of the transition portion.

13. The endoscopic device of claim 11, wherein the holder further comprises a transition portion, a projection area of the first body along an extending direction of the cable is greater than a projection area of the second body along the extending direction of the cable, the first body comprises a first part adjacent to the second surface and a second part adjacent to the third surface, the transition portion is connected to the first part of the first body and the second body, and the transformation portion is connected to the second part of the first body and the second body.

14. The endoscopic device of claim 11, wherein the conducting track comprises a first track component, a second track component and a via component, the first track component is routed from the first surface to one of the third surface and the transformation portion via at least an outer surface of the transformation portion, the second track component is disposed on the second surface, the via component comprises a first conducting structure and a second conducting structure, the first conducting structure is adjacent to the one of the third surface and the transformation portion, and the second conducting structure is adjacent to the second surface and electrically connected to the first conducting structure, the first track component and the second track component.

15. The endoscopic device of claim 11, wherein a groove is formed on the second surface and at least partially accommodates the conducting track and the cable.

16. The endoscopic device of claim 11, wherein the endoscopic image capturing assembly further comprises a light emitting component disposed on a lateral side of the holder.

17. The endoscopic device of claim 11, wherein the endoscopic image capturing assembly further comprises an adaptor connected to the cable and the holder and electrically connected between the terminal of the cable with the conducting track.

18. The endoscopic device of claim 11, wherein the endoscopic image capturing assembly further comprises a lens set assembled with the image sensing device, and an optical axis of the lens set is parallel to an extending direction of the cable.

19. An endoscopic image capturing assembly comprising:
an image sensing device;
a cable;
a conducting track;
a passive electronic component;
a sleeve structure; and
a holder comprising a first body, a second body, a transformation portion, a first surface, a second surface perpendicular to the first surface, a third surface and at least one continuous outer surface located between and connected to the first surface and the second surface;
wherein the first surface is formed on the first body, the second surface and the third surface are formed on the second body and located opposite to each other, the transformation portion is formed between the first body and the third surface, and an accommodating notch is formed on the transformation portion;
wherein the image sensing device is mounted on the first surface and comprises an electrical connecting component;
wherein the conducting track is continuously formed from the first surface to the second surface of the holder along the at least one continuous outer surface of the holder and routed along a wall of the accommodating notch, two ends of the conducting track are respectively located on the first surface and the second surface of the holder, and the conducting track is electrically connected to the electrical connecting component;
wherein the cable is mounted on the second surface, a terminal of the cable is electrically connected to the conducting track, so that the terminal of the cable is electrically connected to the electrical connecting component by the conducting track;
wherein the passive electronic component is disposed on the holder, and the passive electronic component is at least partially disposed in the accommodating notch and electrically connected to the conducting track;
wherein the sleeve structure is connected to an end of the second body away from the first body, and the cable passes through the sleeve structure.

* * * * *